United States Patent
Stripp

(10) Patent No.: US 10,073,069 B2
(45) Date of Patent: Sep. 11, 2018

(54) SYSTEMS AND METHODS TO DETERMINE BODY DRUG CONCENTRATION FROM AN ORAL FLUID

(71) Applicant: Sterling Healthcare Opco, LLC, East Northport, NY (US)

(72) Inventor: Richard Stripp, East Northport, NY (US)

(73) Assignee: Cordant Research Solutions, LLC, Denver, CO (US)

( * ) Notice: Subject to any disclaimer, the term of this patent is extended or adjusted under 35 U.S.C. 154(b) by 33 days.

(21) Appl. No.: 14/785,608

(22) PCT Filed: Apr. 21, 2014

(86) PCT No.: PCT/US2014/034810
§ 371 (c)(1),
(2) Date: Oct. 19, 2015

(87) PCT Pub. No.: WO2014/176167
PCT Pub. Date: Oct. 30, 2014

(65) Prior Publication Data
US 2016/0069847 A1    Mar. 10, 2016

Related U.S. Application Data

(60) Provisional application No. 61/815,205, filed on Apr. 23, 2013.

(51) Int. Cl.
| | | |
|---|---|---|
| *G01N 33/48* | (2006.01) | |
| *G01N 30/86* | (2006.01) | |
| *G01N 30/72* | (2006.01) | |
| *G01N 33/487* | (2006.01) | |
| *A61B 10/00* | (2006.01) | |
| *G06G 7/58* | (2006.01) | |
| *G01N 30/00* | (2006.01) | |
| *G01N 30/08* | (2006.01) | |

(52) U.S. Cl.
CPC ......... *G01N 30/86* (2013.01); *A61B 10/0051* (2013.01); *A61B 10/0096* (2013.01); *G01N 30/7233* (2013.01); *G01N 30/8675* (2013.01); *G01N 33/48714* (2013.01); *A61B 2010/0006* (2013.01); *A61B 2010/0009* (2013.01); *G01N 2030/009* (2013.01); *G01N 2030/085* (2013.01)

(58) Field of Classification Search
None
See application file for complete search history.

(56) References Cited

U.S. PATENT DOCUMENTS

| | | |
|---|---|---|
| 3,783,104 A | 1/1974 | Henshilwood et al. |
| 3,918,435 A | 11/1975 | Beall et al. |
| 4,175,008 A | 11/1979 | White |
| 4,387,725 A | 6/1983 | Mull |
| 4,492,305 A | 1/1985 | Avery |
| 4,707,450 A | 11/1987 | Nason |
| 4,749,655 A | 6/1988 | Monthony et al. |
| 4,803,998 A | 2/1989 | Kezes et al. |
| 5,010,473 A | 4/1991 | Jacobs |
| 5,096,062 A | 3/1992 | Burkardt et al. |
| 5,268,148 A | 12/1993 | Seymour |
| 5,334,502 A | 8/1994 | Sangha |
| 5,335,673 A | 8/1994 | Goldstein et al. |
| 5,376,337 A | 12/1994 | Seymour |
| 5,380,492 A | 1/1995 | Seymour |
| 5,394,626 A | 3/1995 | Brown |
| 5,494,646 A | 2/1996 | Seymour |
| 5,532,131 A | 7/1996 | Douglas |
| 5,609,160 A | 3/1997 | Bahl et al. |
| 5,714,341 A | 2/1998 | Thieme et al. |
| 5,786,227 A | 7/1998 | Charlton |
| 5,786,228 A | 7/1998 | Charlton |
| 5,830,154 A | 11/1998 | Goldstein et al. |
| 5,830,410 A | 11/1998 | Thieme et al. |
| 5,968,746 A | 10/1999 | Schneider |
| 5,981,300 A | 11/1999 | Moll et al. |
| 6,008,056 A | 12/1999 | Thieme |
| 6,303,064 B1 | 10/2001 | Abrams et al. |

(Continued)

FOREIGN PATENT DOCUMENTS

| | | |
|---|---|---|
| WO | 1994/18892 | 9/1994 |
| WO | 2008/012566 | 1/2008 |
| WO | 2008/139324 | 11/2008 |

OTHER PUBLICATIONS

AIT Laboratories, "Blood Analysis for Compliance Testing," published online Jun. 23, 2011. Retrieved from: <URL:https://web.archive.orglweb/20110623204111/http://www.aitlabs.com/compliancetesting-blood.aspx>.
Australian Patent Office, Examination Report No. 1 for Australian Patent Application No. 2014257328, dated Aug. 28, 2017, 4 pages.
Dipiro, J. T., et al., Concepts in Clinical Pharmacokinetics, published online 2005, Fourth Edition, American Society of Health-System Pharmacists: Bethesda, MD. Retrieved from: <URL:http://uqu.edu.saifiles2/tiny_mce/plugins/filemanager/files/4350170/concept-in-clinical-pharmacokinetic.pdf>.
International Search Report and the Written Opinion of the International Searching Authority, or the Declaration for PCT/US17/17476, issued by International Searching Authority dated May 5, 2017. 8 pages.

*Primary Examiner* — Eric S Dejong
(74) *Attorney, Agent, or Firm* — Perkins Coie LLP

(57) ABSTRACT

Oral fluid for drug testing has several advantages over other specimens: (1) It may be collected noninvasively and under direct supervision; (2) its drug concentration reflects blood-drug concentrations; and (3) it can be processed by conventional drug screening and confirmation methods. This technology provides a system that measures the quantity of a drug (without needing a priori knowledge of the drug) in an oral fluid specimen and translates this level to a blood plasma drug concentration. The method first measures the concentration of a drug in an oral fluid sample. Next, a processor calculates the blood plasma concentration from the measured oral fluid drug concentration. Finally, this blood plasma drug level is utilized to calculate a total body drug concentration.

8 Claims, 9 Drawing Sheets

(56) References Cited

U.S. PATENT DOCUMENTS

| | | |
|---|---|---|
| 6,303,081 B1 | 10/2001 | Mink et al. |
| 6,391,261 B1 | 5/2002 | Liang |
| 6,531,096 B1 | 3/2003 | Deveney et al. |
| 6,544,196 B2 | 4/2003 | Caillouette |
| 6,875,185 B2 | 4/2005 | Wong et al. |
| 7,108,662 B2 | 9/2006 | Miller et al. |
| 7,300,632 B2 | 11/2007 | Sugiyama et al. |
| 7,314,453 B2 | 1/2008 | Kuo |
| 7,387,899 B1 | 6/2008 | D'Angelo |
| 7,560,272 B2 | 7/2009 | Ramsey et al. |
| 7,648,681 B2 | 1/2010 | Meyer et al. |
| 7,779,666 B2 | 8/2010 | Johansson et al. |
| 7,837,939 B2 | 11/2010 | Tung et al. |
| 7,850,922 B2 | 12/2010 | Gallagher et al. |
| 7,854,895 B2 | 12/2010 | Gallagher et al. |
| 7,879,293 B2 | 2/2011 | Niedbala et al. |
| 7,977,107 B2 | 7/2011 | Day et al. |
| 7,998,757 B2 | 8/2011 | Darrigrand et al. |
| 8,062,908 B2 | 11/2011 | Mink et al. |
| 8,067,243 B2 | 11/2011 | Erfurth et al. |
| 8,083,094 B2 | 12/2011 | Caulfield et al. |
| 8,278,091 B2 | 10/2012 | Rutter et al. |
| 8,322,565 B2 | 12/2012 | Caulfield et al. |
| 8,454,903 B2 | 6/2013 | Brewster et al. |
| 8,470,230 B2 | 6/2013 | Caulfield et al. |
| 8,486,353 B2 | 7/2013 | Wu et al. |
| 8,491,832 B2 | 7/2013 | Gooden et al. |
| 8,492,136 B2 | 7/2013 | Carlisle et al. |
| 8,504,387 B1 | 8/2013 | O'Meara |
| 8,551,016 B2 | 10/2013 | Slowey et al. |
| 8,673,239 B2 | 3/2014 | Niedbala et al. |
| 8,758,703 B2 | 6/2014 | Shaw et al. |
| 8,865,088 B2 | 10/2014 | Brewster et al. |
| 8,865,458 B2 | 10/2014 | Ramsey et al. |
| 8,871,155 B2 | 10/2014 | Wu et al. |
| 2003/0059947 A1 | 3/2003 | Takagi et al. |
| 2005/0171449 A1 | 8/2005 | Suslick et al. |
| 2006/0084181 A1 | 4/2006 | Farquharson et al. |
| 2008/0255765 A1 | 10/2008 | Akhlaghi et al. |
| 2008/0318322 A1 | 12/2008 | Akhlagi et al. |
| 2009/0024060 A1 | 1/2009 | Darrigrand et al. |
| 2010/0291693 A1 | 11/2010 | Elwell et al. |
| 2012/0046628 A1 | 2/2012 | Wei et al. |
| 2012/0071789 A1 | 3/2012 | Jowett et al. |
| 2012/0186200 A1 | 7/2012 | Jones et al. |
| 2012/0192628 A1 | 8/2012 | Liu et al. |
| 2013/0015346 A1 | 1/2013 | Black |
| 2013/0158431 A1 | 6/2013 | Aronowitz |
| 2013/0209993 A1 | 8/2013 | Aronowitz |
| 2013/0302219 A1 | 11/2013 | Li et al. |
| 2014/0316302 A1 | 10/2014 | Nonnemacher et al. |
| 2015/0308994 A1 | 10/2015 | Hicks John et al. |

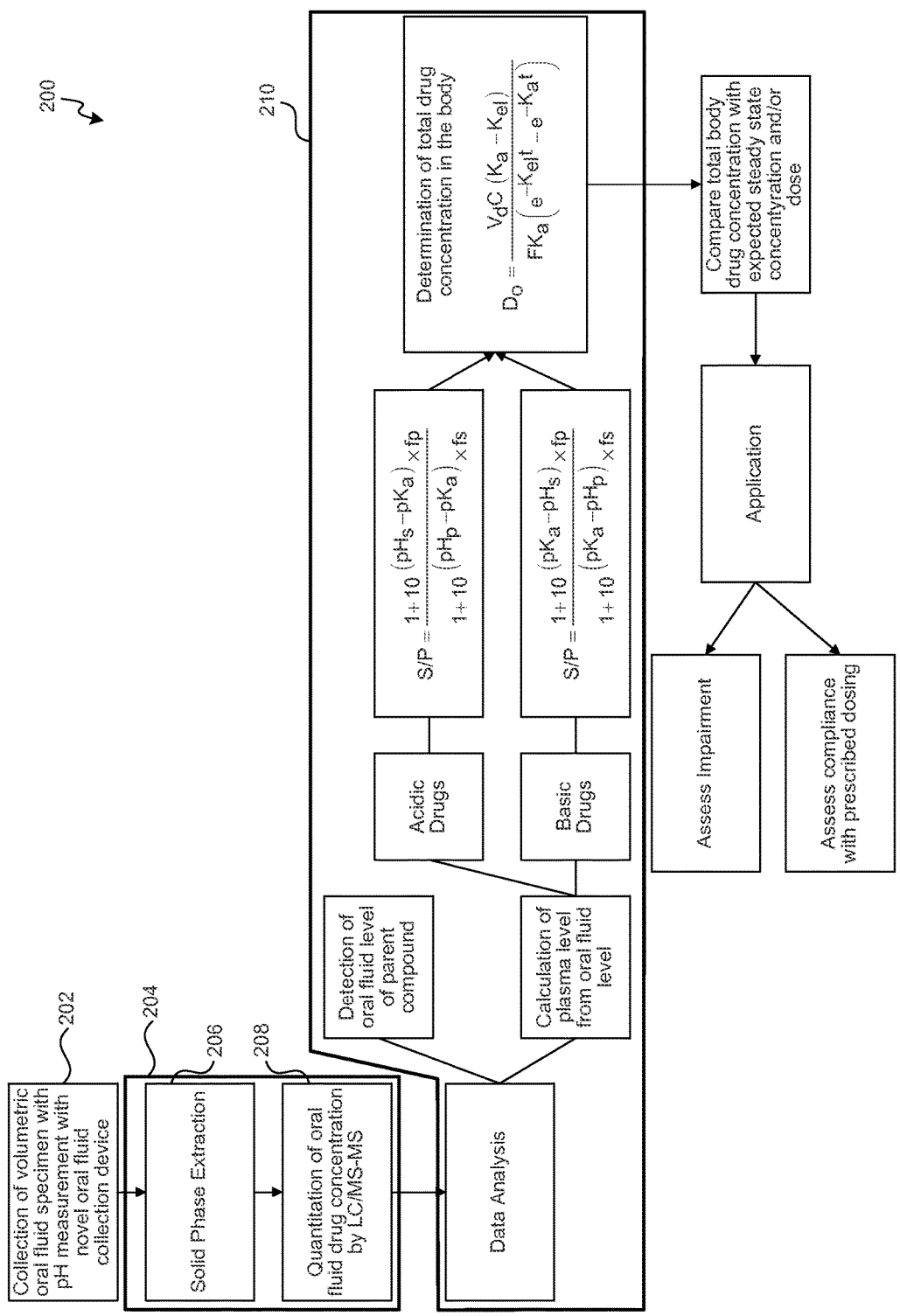
FIG. 2. Outline of the System

| Determination of plasma drug concentrations based on oral fluid analysis for acidic drugs | |
|---|---|
| $$S/P = \frac{1+10^{(pH_s - pK_a)} \times fp}{1+10^{(pH_p - pK_a)} \times fs}$$ | S = Saliva drug concentration<br>P = Plasma drug concentration<br>$pH_s$ = pH of saliva (to be determined at the time of collection)<br>$pH_p$ = pH of plasma (assumed to be 7.4)<br>$pK_a$ = Dissociation constant of a drug (referenced in literature)<br>fp = free fraction of drug in plasma (referenced in literature)<br>fs = free fraction of drug in saliva (negligible; assumed to be 1) |

*FIG. 3. Determination of plasma drug concentrations based on oral fluid analysis for acidic drugs*

| Determination of plasma drug concentrations based on oral fluid analysis for basic drugs | |
|---|---|
| $$S/P = \frac{1+10^{(pK_a - pH_s)} \times fp}{1+10^{(pK_a - pH_p)} \times fs}$$ | S = Saliva drug concentration<br>P = Plasma drug concentration<br>$pH_s$ = pH of saliva (to be determined at the time of collection)<br>$pH_p$ = pH of plasma (assumed to be 7.4)<br>$pK_a$ = Dissociation constant of a drug (referenced in literature)<br>fp = free fraction of drug in plasma (referenced in literature)<br>fs = free fraction of drug in saliva (negligible; assumed to be 1) |

*FIG. 4. Determination of plasma drug concentrations based on oral fluid analysis for basic drugs*

| Determination of total body drug concentration (minimum dosage) consumed based on plasma drug concentrations | |
|---|---|
| $$D_o = \frac{V_d C (K_a - K_{el})}{F K_a \left( e^{-K_{el} t} - e^{-K_a t} \right)}$$ | $D_o$ = Original dosage taken<br>$V_d$ = Volume of distribution of drug (referenced in literature) x body weight of donor in kilograms<br>C = Plasma drug concentration<br>$K_a$ = Absorption constant of drug (referenced in literature)<br>$K_{el}$ = Elimination of constant of drug (referenced in literature)<br>F = Bioavailability of drug (referenced in literature)<br>t = Elapsed time between dosage and specimen collection |

*FIG. 5. Determination of minimum dosage consumed based on plasma drug concentrations*

SYSTEMS AND METHODS TO DETERMINE BODY DRUG CONCENTRATION FROM AN ORAL FLUID

CROSS-REFERENCE TO RELATED PATENT APPLICATIONS

The present application claims priority to U.S. Provisional Patent Application Ser. No. 61/815,205, filed Apr. 23, 2013, the disclosure of which is incorporated herein by reference as if set out in full.

FIELD OF THE INVENTION

The technology of the present application relates generally to correlating the quantitative measurement of drugs in oral fluid to total body drug concentrations and more specifically uses the quantitative measurement of drug concentration in the oral fluid specimens and determines the blood equivalent plasma drug concentration using pharmacokinetic calculations. From this blood equivalent plasma drug concentration, the total body drug concentration, and the assessment of the drug dose required to produce this concentration, is determinable.

BACKGROUND

Historically, urine has been utilized as the primary specimen for the detection of drug use in standard toxicology protocols and drug monitoring programs. The monitoring ensures compliance with treatment regimens and assess potential drug abuse. In both scenarios, the analysis of urine samples primarily targets the metabolite(s) of drugs in the body. Detection of these compounds is facilitated by the relatively high concentration of analyte present in the urine specimen in addition to a reasonably long detection window. However, urine drug testing is limited by the fact that results solely indicate past exposure to the detected compounds. Urine is not an acceptable matrix for determining impairment or pharmacological effects, or to estimate dose compliance based on drug concentrations. Currently, blood is the preferred specimen for assessing impairment based on biologically active drug levels in an individual or determinations as to the minimum dose consumed to produce the corresponding concentrations in the body.

As explained, urine cannot provide a satisfactory sample for analysis to determine impairment, pharmacological effects, or dose compliance. Thus, against this background, improved systems and methods to determine body drug concentration from an oral fluid are desirable.

SUMMARY

This Summary is provided to introduce a selection of concepts in a simplified form that are further described below in the Detailed Description. This Summary, and the foregoing Background, is not intended to identify key aspects or essential aspects of the claimed subject matter. Moreover, this Summary is not intended for use as an aid in determining the scope of the claimed subject matter.

The technology of the present application describes a system, which provides an interpretative measure to assess plasma drug levels from an oral fluid drug test and correlate the dose to the calculated plasma level. In addition to determining the blood equivalent plasma concentration of one or more drugs, this method has application to infer potential pharmacological effects, dose compliance, or drug impairment from an oral fluid drug test (that can be collected onsite). The results generated from this technology may aid in the interpretation of oral fluid drug concentrations as a means to determine if the oral fluid drug level is consistent with a dosage consumed or what effects (impairment or otherwise) may be seen in an individual with a specific drug amount in the body. Using a noninvasive, volumetric oral fluid collection device that also measures pH at the time of collection, an adequate sample can be rapidly obtained. A processor uses the measured oral fluid drug concentration and pharmacokinetic variables to provide a plasma drug level and a minimum dosage required to obtain a corresponding oral fluid drug concentration equivalent.

These and other aspects of the present system and method will be apparent after consideration of the Detailed Description and Figures herein.

DRAWINGS

The technology of the present application will be further explained with reference to the drawing figures reference below, wherein like structures may be referred to by like numerals throughout the several views thereof.

FIG. 2 illustrates an exemplary system using the oral fluid to determine body drug concentration consistent with the technology of the present application.

FIG. 3 is an exemplary algorithm to calculate oral fluid/plasma ratio for acidic drugs consistent with the technology of the present application.

FIG. 4 is an exemplary algorithm to calculate oral fluid/plasma ratio for basic drugs consistent with the technology of the present application.

FIG. 5 is an exemplary algorithm to calculate total body concentration of the drug from the plasma concentration consistent with the technology of the present application.

Figure 1:
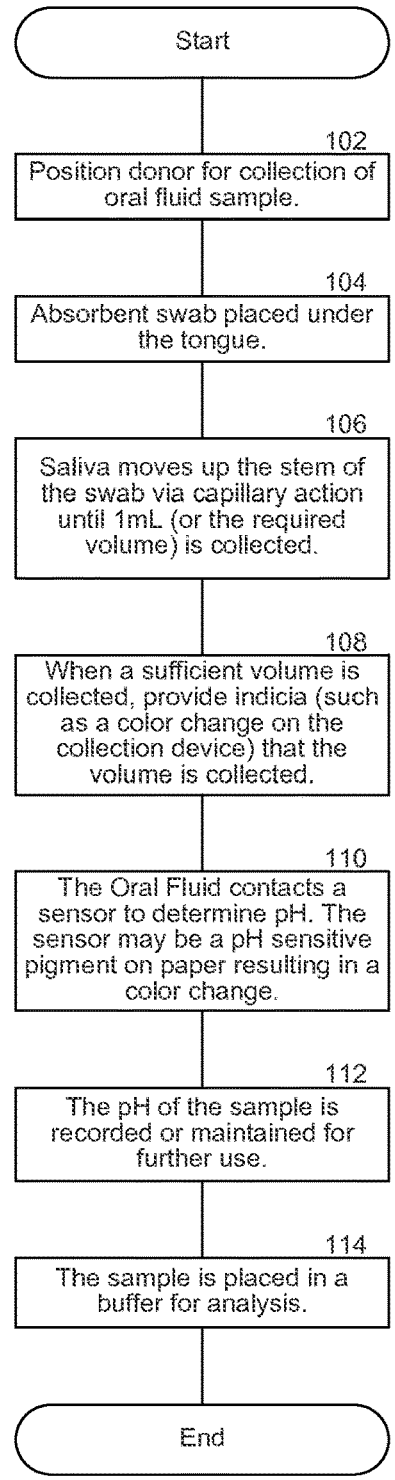
FIG. 1 illustrates a methodology for collecting a volume of oral fluid and measuring the pH of the oral fluid at the time of collection consistent with the technology of the present application.

While the above-identified drawing figures set forth one or more exemplary embodiments, other embodiments of the present invention are also contemplated, as noted throughout. The technology of the present application is described by way of representative examples and should not be construed as limiting. Numerous other modifications and embodiments within the spirit and scope of the technology of the present application are incorporated herein.

DETAILED DESCRIPTION

The technology of the present application will now be described more fully below with reference to the accompanying figures, which form a part hereof and show, by way of illustration, specific exemplary embodiments. These embodiments are disclosed in sufficient detail to enable those skilled in the art to practice the technology of the present application. However, embodiments may be implemented in many different forms and should not be construed as being limited to the embodiments set forth herein. The following detailed description is, therefore, not to be taken in a limiting sense.

The technology of the present application is described with specific reference to using an oral fluid sample to determine total body drug concentration. However, the technology described herein may be used for other applications where oral fluid, perspiration, or the like may be used to determine concentrations of chemicals, organisms, or the like in blood plasma. Additionally, various embodiments of the technology may omit, substitute, or add components as appropriate. Methods of using the technology are disclosed herein, but the methods may be performed in an order different than that described, and various steps may be added, omitted, or combined. Finally, the technology of the present application will be described with relation to exemplary embodiments. The word "exemplary" is used herein to mean "serving as an example, instance, or illustration." Any embodiment described herein as "exemplary" is not necessarily to be construed as preferred or advantageous over other embodiments. Additionally, unless specifically identified otherwise, all embodiments described herein should be considered exemplary.

As described above, urine has been the specimen of choice for drug testing purposes. The use of urine as a method of drug monitoring comes with certain disadvantages. For example, urine collection tends to be more invasive or embarrassing (particularly for observed collection) and samples are susceptible to adulteration (dilution, oxidants etc.) or substitution. Furthermore, drug concentrations in urine are only illustrative of past drug use. Analytical results cannot be used for determining levels of impairment or to assess the dosage taken, due to the fact that urinary drug concentrations do not directly reflect blood levels in the body.

An alternate specimen type with the potential to allow for total drug in the body determinations without the need to draw a blood sample is oral fluid. Oral fluid, sometimes called mixed saliva, comes from three major and multiple minor salivary glands. Oral fluid may comprise the mixed saliva from multiple glands and other constituents in the mouth including plasma electrolytes (K+, Na+, Cl− Bicarbonate), enzymes, and DNA. Oral fluid is a filtrate of the blood. Thus, it has been determined that oral fluid drug concentrations show predictable ratios as compared to plasma drug concentrations. The predictable plasma:oral fluid drug concentration ratios in addition to pharmacokinetic information allow for the calculation of the minimum dose taken that is required to produce an oral fluid drug concentration. Thus, measurement of an oral fluid drug level will allow for the determination of the corresponding plasma blood equivalent plasma drug concentration and subsequently, the minimum dose required to produce this amount and if the concentration corresponds to the expected steady state level of the drug in the blood based on provided dosing regimen.

Oral fluid has the advantage of being very simple to collect and difficult to adulterate. Collections are not invasive and can be easily observed to ensure the validity of the sample. Drug incorporation into oral fluid occurs rapidly after ingestion, allowing for detection of very recent drug use. Because the drug in oral fluid reflects that which is in the plasma, the parent drug is more commonly detected as compared to urine, which tends to have higher concentration of metabolites. Thus, for drugs where metabolites are detectable in urine for long periods after abstinence (e.g. THC), measurement in oral fluid allows for detection of the parent drug that reflects more recent drug use. Furthermore, correlation of drug concentrations in oral fluid and plasma allow for the establishment of concentration ratios. This correlation will serve to predict the amount of drug in the body and ultimately lead to the determination of the minimum amount of drug a patient has taken to achieve the measured oral fluid concentration. Thus providing the capability of calculating the minimum original dose of drug (taken or administered) from the concentration in oral fluid.

The concentration of a drug in the oral fluid along with knowledge of several pharmacokinetic properties of the drug, including, but not limited to, pKa, volume of distribution, absorption constant, elimination constant, and bioavailability together with information relating to pH of the saliva, and elapsed time between dosage and specimen collection allow the prediction of plasma concentration, body concentration, and minimum dose. This information allows for assessment of compliance with a drug regimen. Additionally, it may provide information about the amount of biologically active drug in the body.

Oral Fluid Specimen Collection

With reference now to FIG. 1, an exemplary methodology 100 for collecting oral fluid will be described. First, the donor (sometimes referred to as subject, patient, person, or the like) is positioned to allow retrieval of the oral fluid sample, step 102. Next, an oral fluid collection device is placed in the donor's mouth, step 104. The collection device in one exemplary embodiment may be an absorbent swab placed under the tongue. One particularly useful collection device that has been developed is shown and described in FIG. 6. In this exemplary embodiment, the oral fluid collection device collects about 1 mL of neat oral fluid from the donor. Generally, the term about or approximately in the present application means within an acceptable tolerance, such as, for example, ±10% or the like. Volumetric collection is required for quantitative analysis when analyzed from a buffer solution. Oral fluid may be absorbed by the collection device by allowing saliva to move up the stem of a collection device via capillary action, step 106. When a sufficient amount of oral fluid is collected, the collection device provides indicia that the required collection amount has been collected, step 108. The indicia indicating the required volume is collected may be by a color change on a collection adequacy indicator or the like. Alternatively, an alpha/numeric display may be provided or an audio alert, such as a beep. Determining salivary pH is completed next or substantially at the same time as the required volume is collected, step 110. The pH of the oral fluid may be determined by a pH sensitive pigment or by other means including, for example, a sensor or the like. The pH indicia may be combined or separate from the indicia for volume and may include the same or different indicators. For example, the volume of the sample may be provided by a color strip whereas the pH may be provided by an audio. The collection device may be provided with a display that displays both the volume and the pH in certain embodiments. The pH will then be recorded or otherwise maintained for later use, step 112. In this exemplary embodiment, the donor will provide a sample by placing the collector swab under his or her tongue until the indicator changes color. The swab is then placed in 3 mL of oral fluid extraction buffer that promotes stabilization of the drug, preventing bacterial growth, and facilitates efficient extraction of the drugs and/or metabolites from the adsorbent swab, as is further explained below, step 114. Specimens may be aliquoted for analysis, and any remaining sample may be transferred to long-term storage at, for example, a storage temperature of between about −20 to about 0° C. The collected oral fluid may be referred to as a sample or a specimen interchangeably herein.

The System

With reference now to FIG. 2, a system 200 for determining total body drug concentration from the collected oral fluid sample is described. The system 200 includes a collection device 202, capable of the features described above. The collection device 202 provides a sample to drug concentration analysis engine 204. The drug concentration analysis engine detects types and concentrations of drugs even without a priori knowledge of the drugs. The drug concentration analysis engine 204 may receive the required sample from collection device 202 via, for example, a pipette transfer, or the sample collection device may be releasably attached to the drug concentration analysis engine 204 to place the collection device 202 sample reservoir in fluid communication with the drug concentration analysis engine 204. In one exemplary embodiment, the drug concentration analysis engine 204 may detect drug concentration using a liquid chromatography-mass spectrometry processor. In this case, the drug concentration analysis engine 204 includes a solid phase extraction module 206 and an identification module 208. Once the identification module 208 identifies the drug and the concentration of the drug in the oral fluid, the information is provided to a data analysis engine 210 along with information regarding the chemistry of the oral fluid, with particular regard for the pH of the sample. The data analysis engine 210 comprises processor modules to calculate the blood equivalent plasma blood concentration and the total body concentration of the identified drugs. The total body concentration equivalent of the drugs may be used in numerous applications, some of which may be referenced herein. Other applications, however, are within the spirit and scope of the technology of the present application.

Specimen Preparation

Specimens may undergo a sample preparation step in advance of providing the sample to the drug concentration analysis engine, which involves extracting the analyte(s) of interest from biological matrices. This process serves to eliminate any biological material that could potentially affect analytical results. Samples are first treated to disrupt any drug matrix interactions (protein binding, conjugation) and then adjusted to a specific pH with a buffer. Analytes are then extracted from the remaining matrix using solid phase extraction module 206, which may be comprised of cartridges that are mixed-mode cationic exchange columns. This technique uses the specific binding of ionized drug molecules to the extraction cartridge packing material resulting in strong analyte retention within the column. A series of aqueous and organic wash steps may be used to assist in removing unwanted compounds and matrix components from the sample. Target analytes are then eluted from the solid phase extraction module 206, collected, and analyzed by identification module 208 that may be, for example, a liquid chromatography tandem mass spectrometry (LC/MS-MS) device, although other analysis devices are possible.

Drug Quantitation by Liquid Chromatography Tandem Mass Spectrometry (LC/MS-MS)

In this exemplary embodiment, the specimens are analyzed by the identification module 208 that is a LC/MS-MS device, which allows for accurate and precise analyte identification and quantitation. This analytical technique uses a chromatographic system to separate all of the sample components into discrete peaks and sequentially identifies each compound through mass spectral identification. The chromatographic system is composed of a stationary phase of hydrophobic character (for example, octadecylsilane) and a mobile phase of varying polarity (for example, methanol, water). Specimens are injected into the chromatograph and pumped through the system by flow of the mobile phase. Separation is brought about by differential interactions with the stationary phase based on physical and chemical properties of the individual analytes. The end result is a separation of all of the sample components into discrete bands. As each component elutes from the liquid chromatograph it enters the mass spectrometer. The mass spectrometer is able to first determine an analytes specific molecular weight, called a precursor ion, and subsequently fragment the precursor ion into smaller fragments called product ions. The precursor ion and generated product ions are a specific marker of every analyte of interest. No two compounds will generate completely identical mass spectra. This allows for the identification module 208 to conclusively identify specimen components. Additionally, when specimens are analyzed alongside a series of standards of known concentration, a calibration curve can be generated and quantitative values of identified drugs can be determined.

Data Analysis

The identification module 208 outputs data obtained from the analysis of oral fluid relating to the drug and the drug concentration in the oral fluid. Oral fluid specimens may be used to determine blood equivalent plasma drug concentration and ultimately correlate the derived blood equivalent plasma drug concentration to the minimum dosage of a drug required to produce the measured drug level. FIGS. 3-5 provide algorithms implemented by the data analysis module 210 to automatically correlate the drug concentration in the sample to the blood equivalent plasma drug concentration. When using these equations, plasma pH is assumed to be constant at 7.4 and drug protein binding is assumed to be negligible in the saliva. Therefore, a value of 1 is used for fs. The binding of drugs to plasma proteins varies from drug to drug. However, it remains fairly consistent between individuals. Normally, saliva pH may vary from 6 to 8. If the pH is measured at the time of sample collection, one can modify this variable in the equation and thus derive the blood equivalent plasma drug concentration of a drug given its saliva drug concentration. The percentage of drug and/or metabolite transferred from blood to saliva is primarily dependent on salivary pH. For basic drugs, as the salivary pH decreases, a greater concentration of drug will be ionized, and the oral fluid drug concentration will increase. Minor changes in salivary pH may result in significant changes in the saliva/plasma ratio (S/P ratio). Much of the pharmacokinetic and pharmacodynamic research reported on therapeutic and abused drugs has been based on plasma drug concentrations. Because the S/P ratio can be shown to be predictable using mathematical models, the databases on plasma pharmacokinetic, physiological, and behavioral data may be used to support interpretation of saliva drug concentrations. Mathematical models provide S/P concentration ratios for acidic and basic drugs and the following pharmacokinetic formulas are used to convert the oral fluid drug level to the plasma drug level:

Determination of Plasma Drug Concentrations (Solving for P) Based on Oral Fluid Analysis (Acidic Drugs)

$$S/P = \frac{1 + 10^{(pHs-pKa)} \times fp}{1 + 10^{(pHp-pKa)} \times fs}$$

Determination of Plasma Drug Concentrations (Solving for P) Based on Oral Fluid Analysis (Basic Drugs)

$$S/P = \frac{1 + 10^{(pKa-pHs)} \times fp}{1 + 10^{(pKa-pHp)} \times fs}$$

Where:
S=Saliva drug concentration
P=Plasma drug concentration
pHs=pH of saliva (to be determined at the time of collection)
pHp=pH of plasma (assumed to be 7.4)
pKa=Dissociation constant of a drug (referenced in literature)
fp=Free fraction of drug in plasma (referenced in literature)
fs=Free fraction of drug in saliva (negligible; assumed to be 1)

Once a plasma concentration has been established then the following calculation can be performed:

Determination of Minimum Dosage Consumed Based on Plasma Drug Concentrations $$D_o = \frac{V_d C (K_a - K_{el})}{FKa(e^{-Kelt} - e^{-Kat})}$$

Where:
Do=Original dosage taken
Vd=Volume of distribution of drug (referenced in literature) times the kg body weight of donor
C=Plasma drug concentration
Ka=Absorption constant of drug (referenced in literature)
Kel=Elimination constant of drug (referenced in literature)
F=Bioavailability of drug (referenced in literature)
t=Elapsed time between dosage and specimen collection Using oral fluid-concentrations to determine dosing has at least two advantages: assessing impairment due to bioactive levels of drugs in a forensic setting and the ability to assess compliance with prescribed dosing regimens for clinical treatment without the necessity of drawing blood.

As described above, the pH of the sample is determined and recorded at the time of oral fluid collection. The data analysis engine 210 uses the pH to determine a processing algorithm based on whether the target analyte is acidic or basic (see FIGS. 3 and 4). The fixed variables, such as percentage of plasma protein binding and drug pKa are stored in a memory associated with the data analysis engine 210. Using these data, in addition to saliva drug concentration, the data analysis engine 210 calculates blood equivalent plasma concentration.

As shown in FIG. 5, which is the third formula mentioned above, the minimum dosage required to produce a corresponding plasma concentration is determinable. The basis for this formula is derived from the volume of distribution (Vd) of the drug, which is simply defined as a ratio of the amount of drug in the body to the equivalent drug concentration in plasma. The Vd describes the extent of distribution of drug into target tissues when equilibrium has been established between blood and tissue, before elimination has begun. Based on the physical and chemical properties of the drug, Vd can be influenced by many factors such as the extent of plasma protein binding, lipophilicity, molecular size, and state of ionization. With knowledge of the time interval between last dosage taken and sample collection, as well as plasma drug concentrations, an estimate of minimum dose can be made. Similarly, comparison of the plasma concentration to the known and established steady state concentration of that drug in plasma will provide interpretive information about the dosing of the drug in a person.

Figure 6:
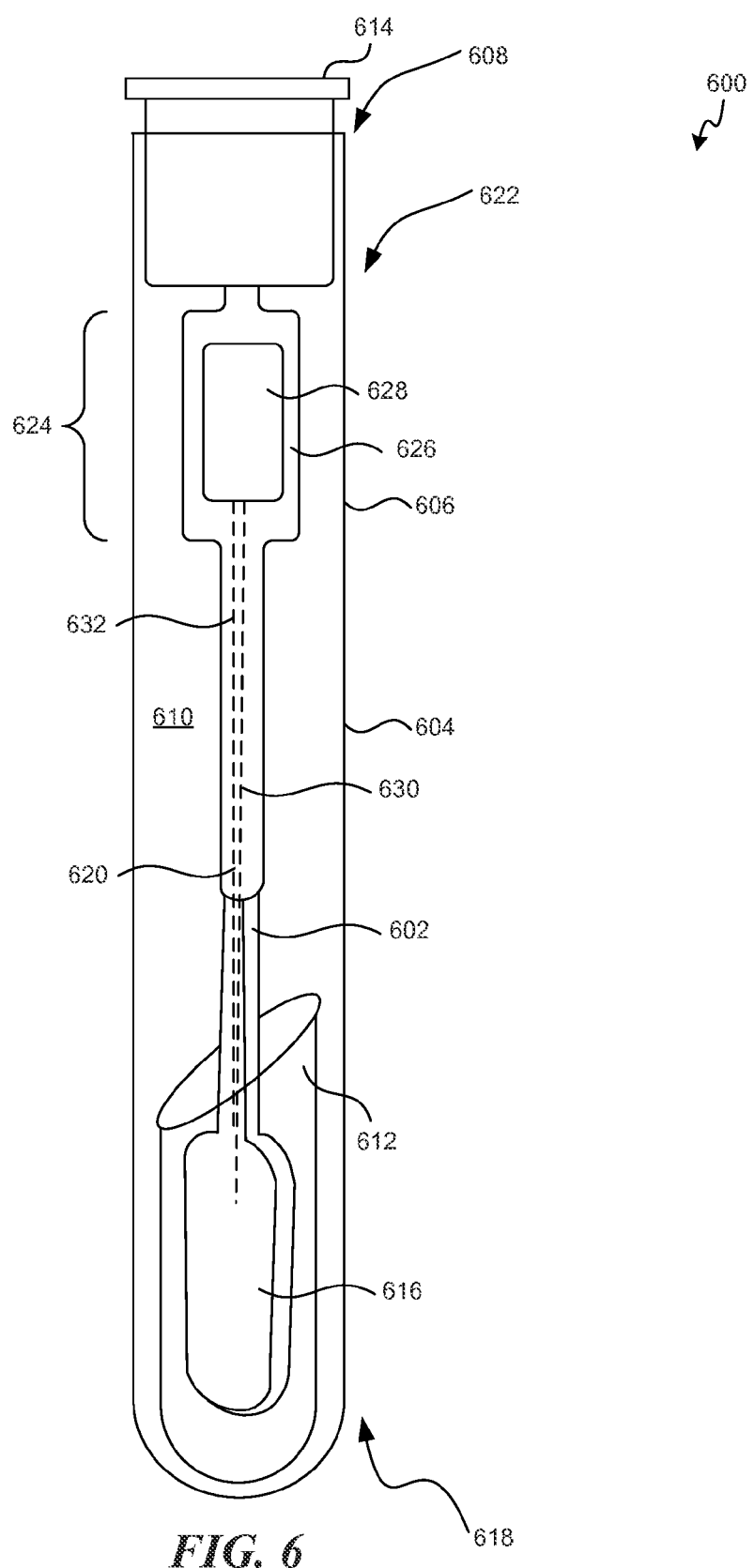
FIG. 6 is an exemplary collection device consistent with the technology of the present application.
Figure 7:
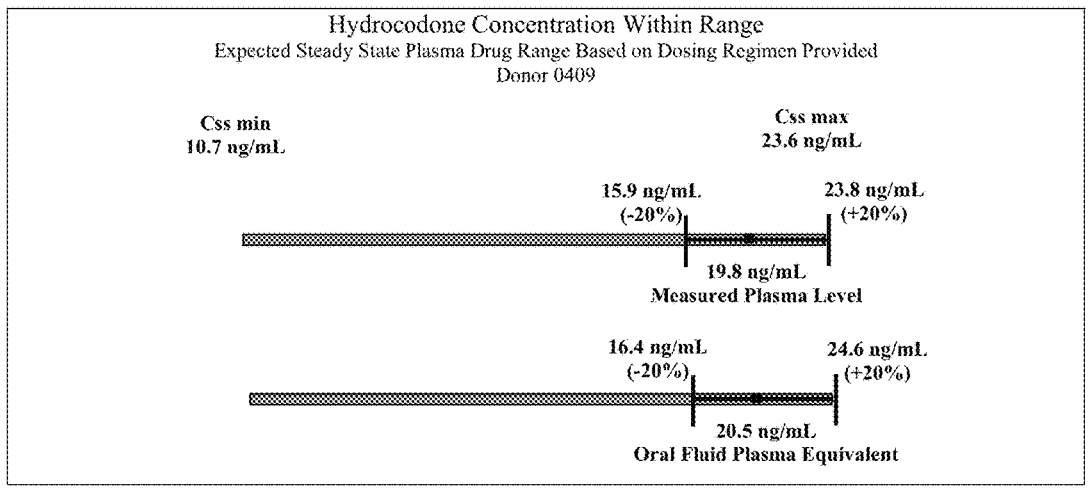
FIG. 7 is a graphical representation of hydrocodone example donors within range.
Figure 8:
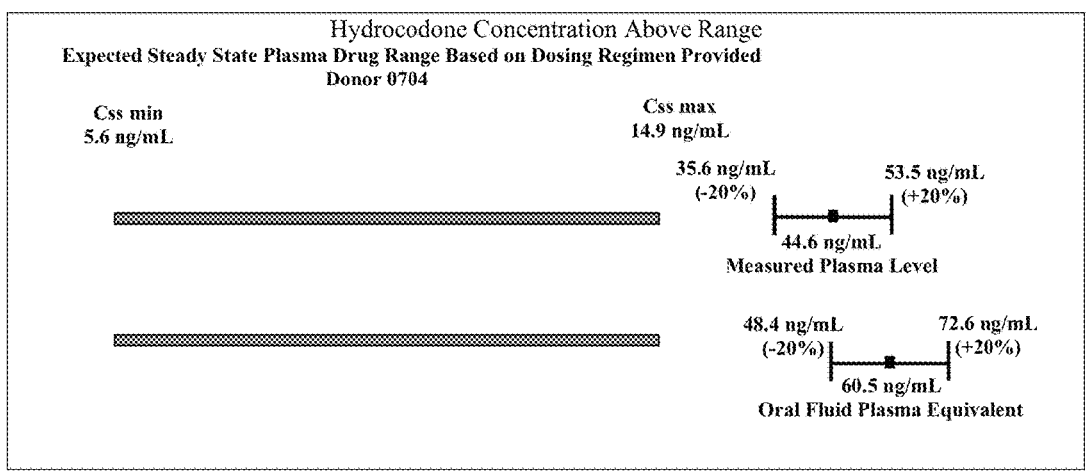
FIG. 8 is a graphical representation of hydrocodone example donors above range.
Figure 9:
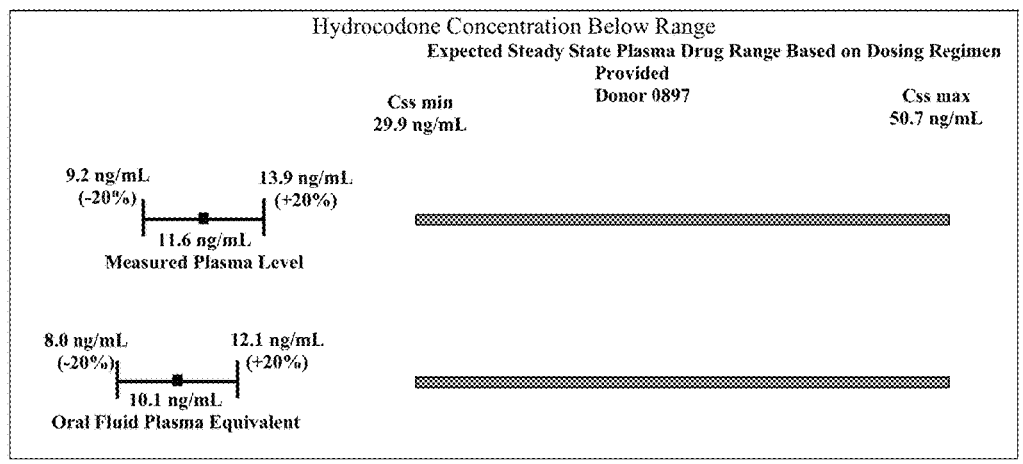
FIG. 9 is a graphical representation of hydrocodone example donors below range.
Figure 10:
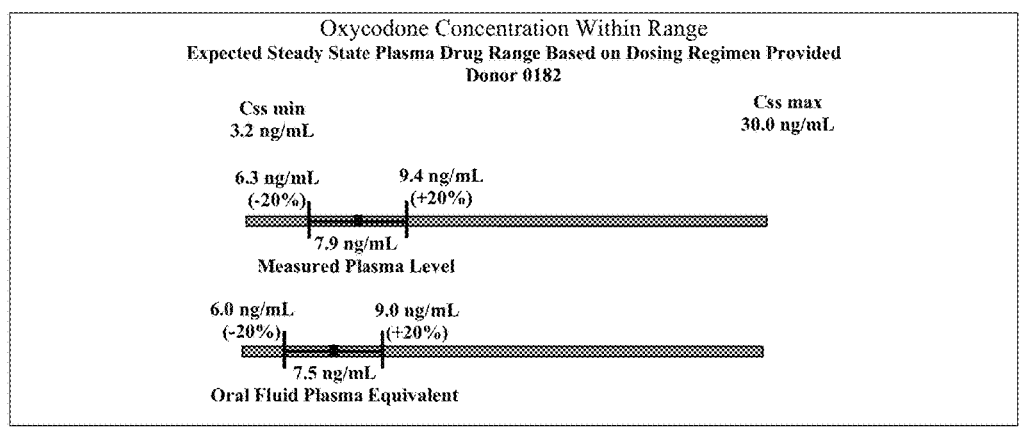
FIG. 10 is a graphical representation of oxycodone example donors within range.
Figure 11:
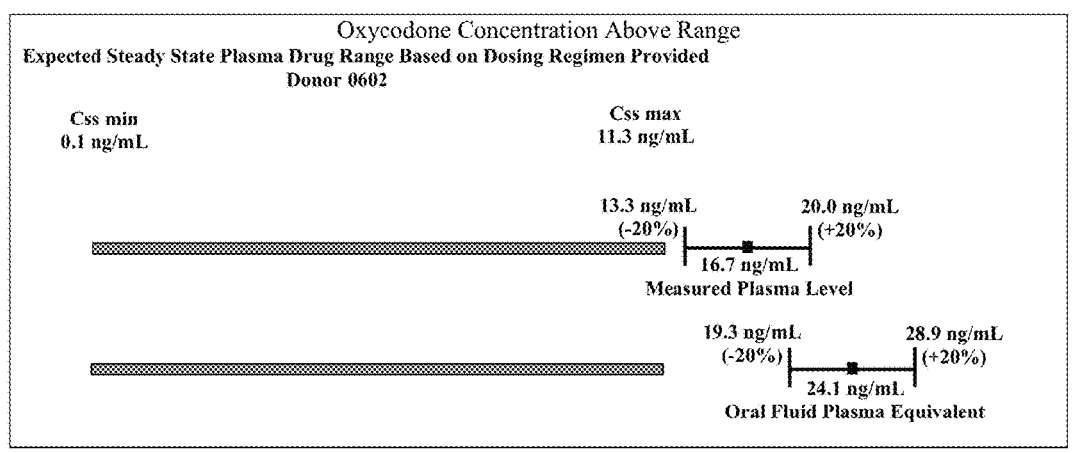
FIG. 11 is a graphical representation of oxycodone example donors above range.
Figure 12:
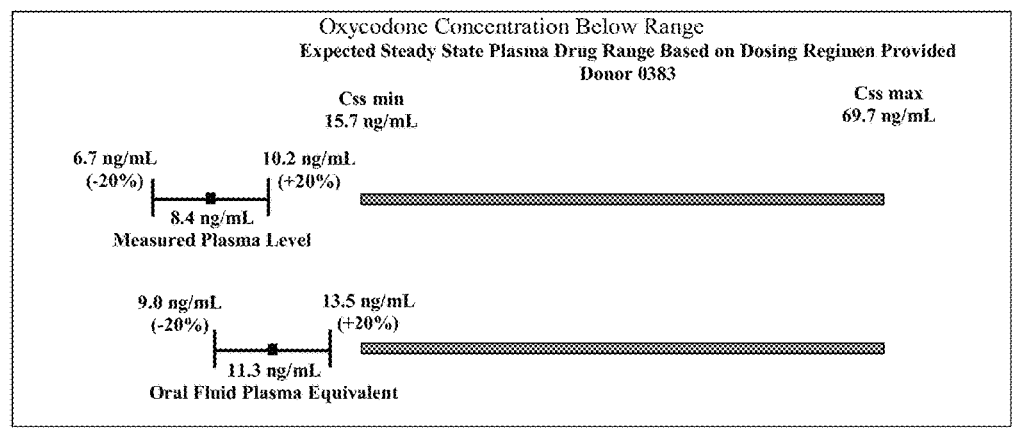
FIG. 12 is a graphical representation of oxycodone example donors below range.
Figure 13:
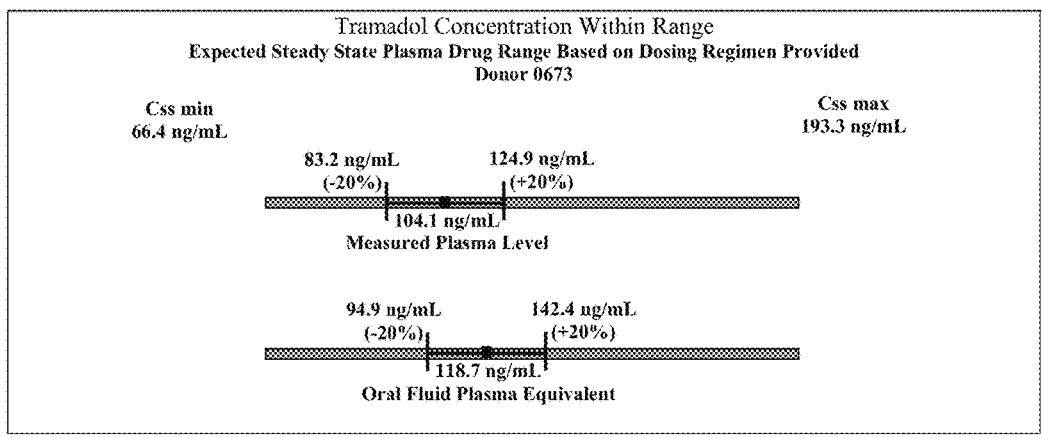
FIG. 13 is a graphical representation of tramadol example donors within range.
Figure 14:
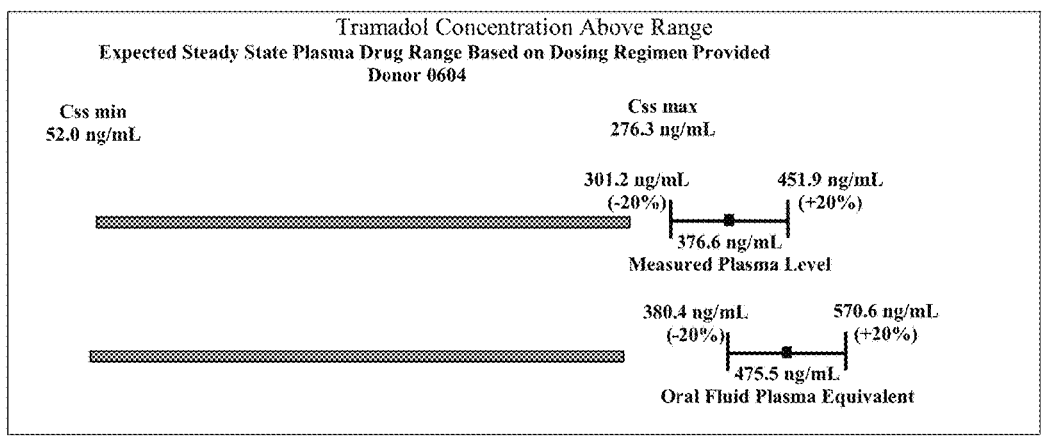
FIG. 14 is a graphical representation of tramadol example donors above range.
Figure 15:
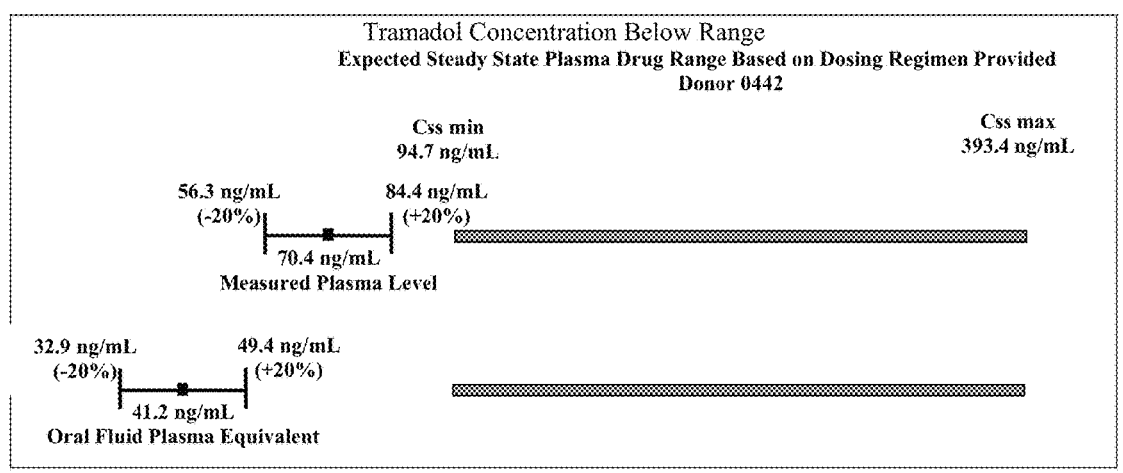
FIG. 15 is a graphical representation of tramadol example donors below range.

As mentioned above, the technology of the present application uses a collection of oral fluid, or saliva, to obtain the information necessary to calculate blood equivalent plasma drug concentration. FIG. 6 shows an exemplary collection and transport device 600. The collection and transport device 600 includes a collection portion 602 and a transport portion 604. The transport portion 604 includes a housing 606 having an opening 608 to allow the collection portion 602 to be inserted into the transport portion 604 subsequent to collecting the sample of oral fluid. The housing 606, as shown, may be a simple test tube or the like. The transport portion 604 has a generally hollow interior 610 that contains a measure of buffer solution 612 (as described above). A topper 614, which may be a cap or plug, is removably secured to the opening 608 of the transport portion 604. The topper 614 prevents the buffer solution 612 from leaking from the hollow interior 610. The topper 614 is removed such that the collection portion 602 may be inserted into the hollow interior 610 subsequent to the collection of the oral fluid. Once the collection portion 602 is inserted into the transport portion 604, the topper 614 is secured to the opening 608. The topper 614 may be secured to the opening 608 using a friction fit, as shown, threads, a snap fit, or the like.

The collection portion 602 includes an absorbent swab 616 at a first end 618 of the collection portion 602. The absorbent swab 616 may be any type of absorbent material, such as a cotton swab, filter paper, a porous fabric material, etc. The absorbent swab 616 is coupled to a handle 620 extending from the absorbent swab towards a second end 622 of the collection portion 602. An indicator 624 is coupled to the handle 620 towards the second end 622 of the collection portion 602. The indicator 624 may have a first indicator 626 and a second indicator 628. The first indicator 626 may be designed to indicate the collection of a particular volume of oral fluid, such by changing color when 1 ml of oral fluid is collected by the absorbent 616. When a sufficient amount of oral fluid is collected, the oral fluid travels along the handle 620, via a fluid conduit 630, which may be a wick or a capillary tube, to the first indicator 626 whereby the oral fluid causes, in one exemplary embodiment, the first indicator 626 to change color indicating an acceptable level of fluid has been collected. The second indicator 628 also is in fluid communication with the absorbent 616, such as via the same fluid conduit 630 or a second fluid conduit 632. The second indicator 628 may indicate the pH of the oral fluid by, for example, a color code or the like. Notice, while shown as a completely separate second fluid conduit 632, the fluid conduits 630 and 632 may be merged in part and separated in part forming, for example, a Y-shape to provide oral fluid to both indicators, but using a common conduit from the absorbent 616 until a branching to provide two separate fluid streams to the indicators 626 and 628. Moreover, while the indicators are shown and described as indicators that change color, the indicators could be electronic displays, audio, or the like instead of a color strip.

The technology of the present application was applied in several exemplary embodiments as outlined below. The exemplary embodiments relate to specific patients, donors, or people, and specific drugs, metabolites, and the like. However, the examples are provided to exemplify the technology presented herein and are not to be considered limiting. To technology of using oral fluids to determine blood equivalent plasma drug concentrations was tested against actual blood plasma tests as will be explained below.

Donor Calculations

Each donor's drug clearance rate is determined by multiplying the drugs clearance rate (referenced in literature) by the donor's weight (provided).

Determination of donor clearance. Eq. 1

Donor Clearance (L/hr) =

$$\text{Drug Clearance } (L \times hr^{-1} \times kg^{-1}) \times \text{Donor Weight (kg)}.$$

Likewise, each donor's volume of distribution ($DV_d$) is calculated by multiplying the drug volume of distribution ($V_d$) (referenced in literature) by the donor's weight (provided).

Determination of donor volume of distribution Eq. 2

$$DV_d(L) = V_d(L) \times \text{Donor Weight (kg)}.$$

Each donor's steady state drug concentration range is calculated by determining the steady state maximum drug concentration ($C_{ss}$ max) and the steady state minimum drug concentration ($C_{ss}$ min) by the following formulas:

Determination of steady state Eq. 3
maximum plasma drug concentration $$C_{ss}\text{max} = \frac{F \times \text{dose}/1 - e^{-kt}}{DV_d}$$

$C_{ss}$max = Steady state maximum concentration (ng/mL)
$F$ = Fractional bioavailability
$k$ = Fractional rate constant (drug clearance/$V_d$)
$t$ = Dose frequency (hr)
$DV_d$ = Donor volume of distribution (reference Eq. 2).

Determination of steady state Eq. 4
minimum plasma drug concentration $C_{ss}$min = $C_{ss}$max $\times e^{-kt}$
$C_{ss}$min = Steady state minimum concentration (ng/mL)
$k$ = Fractional rate constant (drug clearnace/$V_d$)
$t$ = Dose frequency (hr)

Calculated Values

Each donor provides simultaneous serum and oral fluid samples. The measured serum drug concentration is the LC-MS/MS response ratio of drug to internal standard determined from the individual's provided serum sample. The measured oral fluid drug concentration ratio is the LC-MS/MS response ratio of drug to internal standard determined from the individual's provided oral fluid sample. The oral fluid plasma equivalent is derived from the individual's measured oral fluid drug concentration, salivary pH, as well as various drug parameters referenced in literature.

Determination of plasma drug concentration Eq. 5
based on oral fluid analysis for acidic drugs.

$$S/P = \frac{1 + 10^{(pHs-pKa)} \times fp}{1 + 10^{(pHp-pKa)} \times fs}$$

$S$ = Saliva drug concentration (ng/mL)
$P$ = Plasma drug concentration (ng/mL)
$pH_s$ = pH of saliva
    (to be determined at the time of collection)
$pH_p$ = pH of plasma (assumed to be 7.4)
$pKa$ = Dissociation constant
    of a drug (referenced in literature)
$fp$ = Free fraction of drug in plasma (referenced in literature)
$fs$ = Free fraction of drug
    in saliva (negligible; assumed to be 1).

Determination of plasma drug concentration Eq. 6
based on oral fluid analysis for basic drugs.

$$S/P = \frac{1 + 10^{(pKa-pHs)} \times fp}{1 + 10^{(pKa-pHp)} \times fs}$$

$S$ = Saliva drug concentration (ng/mL)
$P$ = Plasma drug concentration (ng/mL)
$pH_s$ = pH of saliva
    (to be determined at the time of collection)
$pH_p$ = pH of plasma (assumed to be 7.4)
$pKa$ = Dissociation constant
    of a drug (referenced in literature)
$fp$ = Free fraction of drug in plasma (referenced in literature)
$fs$ = Free fraction of drug
    in saliva (negligible; assumed to be 1).

Once the S/P ratio for a drug is calculated using Eq. 5 or Eq. 6, oral fluid plasma equivalent is determined by multiplying the calculated S/P by the measured oral fluid drug concentration determined by LC/MS-MS quantitation, ultimately eliminating the necessity of directly analyzing blood samples to determine donor compliance.

Determination of calculated plasma drug concentration. Eq. 8

Oral fluid plasma equivalent (ng/mL) =

$$\frac{\text{Measured oral fluid drug concentration (ng/mL)}}{\text{Calculated S/P}}.$$

Determination of Compliance

The steady state concentration ranges calculated by Eq. 3 and Eq. 4 provide a drug concentration range unique to each donor. This range is the guideline to determining an individual's compliance with the dosing regimen provided. Both the LC/MS-MS quantitated plasma drug concentration and the oral fluid plasma equivalent determined by Eq. 8 are compared to the steady state range determined. The measured plasma drug concentration can fall within the range, fall above the range, or fall below the range, providing clues to donor compliance. Similarly, the oral fluid plasma equivalent can fall within the range, fall above the range, or fall below the range. There is an agreement in compliance if the measured and the oral fluid plasma equivalent drug concentrations either both fall within the range, both fall above the range, or both fall below the range. These calculations apply to a wide range of therapeutic drugs. FIGS. 7-15 and the following examples illustrate the application of the equations above in a proof of concept study.

Example Calculations Supporting Equations Above in Proof of Concept Study

Hydrocodone Example Calculation

TABLE 1

Hydrocodone pharmacokinetic parameters.
Hydrocodone

| | |
|---|---|
| Clearance (L × hr$^{-1}$ × kg$^{-1}$) | 0.529 |
| Volume of Distribution (L/kg) | 4.0 |
| Fractional Bioavailability | 0.7 |
| Fractional Rate Constant (hr$^{-1}$); "k" | 0.132 |
| Unbound Fraction (fp) | 0.68 |
| pKa | 8.9 |

TABLE 2

Donor information.

| Donor | Salivary pH (pHs) | Dose (mg) | Dosing Frequency (hr) | Weight (kg) |
|---|---|---|---|---|
| 0409 | 6 | 5 | 6 | 67.646 |
| 0704 | 6.6 | 10 | 12 | 147.55 |
| 0897 | 7 | 10 | 4 | 83.99 |

TABLE 3

Donor calculations.

| Donor | Donor Clearance (L/hr) Donor Clearance (L/hr) = Drug Clearance (L × hr$^{-1}$ × kg$^{-1}$) × Donor Weight (kg) | $DV_d$ (L) $DV_d$ (L) = $V_d$ (L) × Donor Weight (kg) |
|---|---|---|
| 0409 | = 0.529 × 67.646<br>= 35.785 L/hr | = 4.0 × 67.646<br>= 270.5 L |
| 0704 | = 0.529 × 147.55<br>= 78.054 L/hr | = 4.0 × 147.55<br>= 590.2 L |

TABLE 4

Calculated steady state maximum plasma hydrocodone concentration.

$$C_{ss}\max = \frac{F \times \text{dose}/1 - e^{-kt}}{DV_d}$$

| Donor 0409 | Donor 0704 | Donor 0897 |
|---|---|---|
| $= \dfrac{0.7 \times 5/1 - e^{-(0.132 \times 6)}}{270.5}$ | $= \dfrac{0.7 \times 10/1 - e^{-(0.132 \times 12)}}{590.2}$ | $= \dfrac{0.7 \times 10/1 - e^{-(0.132 \times 4)}}{335.9}$ |
| = 23.6 ng/mL | = 14.9 ng/mL | = 50.7 ng/mL |

TABLE 5

Calculated steady state minimum plasma hydrocodone concentration.

$$C_{ss}\min = C_{ss}\max \times e^{-kt}$$

| Donor 0409 | Donor 0704 | Donor 0897 |
|---|---|---|
| = 23.6 × $e^{-(0.132 \times 6)}$ | = 14.9 × $e^{-(0.132 \times 12)}$ | = 50.7 × $e^{-(0.132 \times 4)}$ |
| = 10.7 ng/mL | = 3.0 ng/mL | = 29.9 ng/mL |

TABLE 6

Calculated saliva to plasma hydrocodone concentration ratio calculation.

$$S/P = \frac{1 + 10^{(pKa-pHs)} \times fp}{1 + 10^{(pKa-pHp)} \times fs}$$

| Donor 0409 | Donor 0704 | Donor 0897 |
|---|---|---|
| $= \dfrac{1 + 10^{(8.9-6)} \times 0.68}{1 + 10^{(8.9-7.4)} \times 1}$ | $= \dfrac{1 + 10^{(8.9-6)} \times 0.68}{1 + 10^{(8.9-7.4)} \times 1}$ | $= \dfrac{1 + 10^{(8.9-7)} \times 0.68}{1 + 10^{(8.9-7.4)} \times 1}$ |
| = 16.5 | = 4.1 | = 1.6 |

TABLE 7

Hydrocodone LC-MS/MS quantitation.

| Donor | Measured Saliva Hydrocodone Concentration (ng/mL) | Measured Plasma Hydrocodone Concentration (ng/mL) |
|---|---|---|
| 0409 | 341.2 | 19.8 |
| 0704 | 252.7 | 44.6 |
| 0897 | 17.1 | 11.6 |

TABLE 8

Oral fluid plasma equivalent calculation.

$$\text{Oral fluid plasma equivalent (ng/mL)} = \frac{\text{Measured oral fluid drug concentration (ng/mL)}}{\text{Calculated S/P}}$$

| Donor 0409 | Donor 0704 | Donor 0897 |
|---|---|---|
| $=\frac{341.2}{16.5}$ | $=\frac{252.7}{4.1}$ | $=\frac{17.1}{1.6}$ |
| = 20.5 ng/mL | = 60.5 ng/mL | = 10.6 ng/mL |

TABLE 9

Compliance analysis.

| Donor | $C_{ss}$ max (ng/mL) | $C_{ss}$ min (ng/mL) | Measured Hydrocodone Plasma Concentration (ng/mL) | Compliance | Hydrocodone Oral Fluid Plasma Equivalent (ng/mL) | Compliance | Agreement in Compliance |
|---|---|---|---|---|---|---|---|
| 0409 | 23.6 | 10.7 | 19.8 | Within | 20.5 | Within | Agree |
| 0704 | 14.9 | 5.6 | 44.6 | Above | 60.5 | Above | Agree |
| 0897 | 50.7 | 29.9 | 11.6 | Below | 10.1 | Below | Agree |

Expected steady state plasma drug range is calculated based on dosing regimen provided by donor. Maximum steady state concentrations may fall outside therapeutic ranges and approach and/or exceed toxic ranges due to drug tolerance.

Example Calculations Supporting Equations Above in Proof of Concept Study

Oxycodone Example Calculation

TABLE 10

Oxycodone pharmacokinetic parameters.
Oxycodone

| | |
|---|---|
| Clearance (L × hr$^{-1}$ × kg$^{-1}$) | 0.744 |
| Volume of Distribution (L/kg) | 2.0 |
| Fractional Bioavailability | 0.735 |
| Fractional Rate Constant (hr$^{-1}$); "k" | 0.372 |
| Unbound Fraction (fp) | 0.55 |
| pKa | 8.5 |

TABLE 11

Donor information.

| Donor | Salivary pH (pHs) | Dose (mg) | Dosing Frequency (hr) | Weight (kg) |
|---|---|---|---|---|
| 0182 | 5.5 | 5 | 6 | 68.554 |
| 0602 | 5.5 | 5 | 12 | 163.44 |
| 0383 | 5.8 | 10 | 4 | 68.10 |

TABLE 12

Donor calculations.

| Donor | Donor Clearance (L/hr) Donor Clearance (L/hr) = Drug Clearance (L × hr$^{-1}$ × kg$^{-1}$) × Donor Weight (kg) | $DV_d$ (L) $DV_d$ (L) = $V_d$ (L) × Donor Weight (kg) |
|---|---|---|
| 0182 | = 0.744 × 68.554<br>= 51.004 L/hr | = 2.0 × 68.554<br>= 137.1 L |
| 0602 | = 0.744 × 163.44<br>= 121.599 L/hr | = 2.0 × 163.44<br>= 326.8 L |
| 0383 | = 0.744 × 68.10<br>= 50.600 L/hr | = 2.0 × 68.10<br>= 136.2 L |

TABLE 13

Calculated steady state maximum plasma oxycodone concentration.

$$C_{ss}\max = \frac{F \times \text{dose}/1 - e^{-kt}}{DV_d}$$

| Donor 0182 | Donor 0602 | Donor 0383 |
|---|---|---|
| $= \dfrac{0.735 \times 10/1 - e^{-(0.372 \times 6)}}{137.1}$ | $= \dfrac{0.735 \times 5/1 - e^{-(0.372 \times 12)}}{326.8}$ | $= \dfrac{0.735 \times 5/1 - e^{-(0.372 \times 4)}}{136.2}$ |
| = 30.0 ng/mL | = 11.3 ng/mL | = 69.7 ng/mL |

TABLE 14

Calculated steady state minimum plasma oxycodone concentration.
$$C_{ss} \min = C_{ss} \max \times e^{-kt}$$

| Donor 0182 | Donor 0602 | Donor 0383 |
|---|---|---|
| $= 30.0 \times e^{-(0.372 \times 6)}$ | $= 11.3 \times e^{-(0.372 \times 12)}$ | $= 69.7 \times e^{-(0.372 \times 4)}$ |
| $= 3.2$ ng/mL | $= 0.1$ ng/mL | $= 15.7$ ng/mL |

TABLE 15

Calculated saliva to plasma oxycodone concentration ratio calculation.

$$S/P = \frac{1 + 10^{(pKa-pHs)} \times fp}{1 + 10^{(pKa-pHp)} \times fs}$$

| Donor 0182 | Donor 0602 | Donor 0383 |
|---|---|---|
| $= \dfrac{1 + 10^{(8.5-5.5)} \times 0.55}{1 + 10^{(8.5-7.4)} \times 1}$ | $= \dfrac{1 + 10^{(8.5-5.5)} \times 0.55}{1 + 10^{(8.5-7.4)} \times 1}$ | $= \dfrac{1 + 10^{(8.5-5.8)} \times 0.55}{1 + 10^{(8.5-7.4)} \times 1}$ |
| $= 40.5$ | $= 40.5$ | $= 20.3$ |

TABLE 16

Oxycodone LC-MS/MS quantitation.

| Donor | Measured Saliva Oxycodone Concentration (ng/mL) | Measured Plasma Oxycodone Concentration (ng/mL) |
|---|---|---|
| 0182 | 306.4 | 7.9 |
| 0602 | 978.2 | 16.7 |
| 0383 | 230.2 | 8.4 |

TABLE 17

Oral fluid plasma equivalent calculation.

$$\text{Oral fluid plasma equivalent (ng/mL)} = \frac{\text{Measured oral fluid drug concentration (ng/mL)}}{\text{Calculated } S/P}$$

| Donor 0182 | Donor 0602 | Donor 0383 |
|---|---|---|
| $= \dfrac{306.4}{40.5}$ | $= \dfrac{978.2}{40.5}$ | $= \dfrac{230.2}{20.3}$ |
| $= 7.5$ ng/mL | $= 24.1$ ng/mL | $= 11.3$ ng/mL |

TABLE 18

Compliance analysis.

| Donor | $C_{ss}$ max (ng/mL) | $C_{ss}$ min (ng/mL) | Measured Oxycodone Plasma Concentration (ng/mL) | Compliance | Oxycodone Oral Fluid Plasma Equivalent (ng/mL) | Compliance | Agreement in Compliance |
|---|---|---|---|---|---|---|---|
| 0182 | 30.0 | 3.2 | 7.9 | Within | 7.5 | Within | Agree |
| 0602 | 11.3 | 0.1 | 16.7 | Above | 24.1 | Above | Agree |
| 0383 | 69.7 | 15.7 | 8.4 | Below | 11.3 | Below | Agree |

Expected steady state plasma drug range is calculated based on dosing regimen provided by donor. Maximum steady state concentrations may fall outside therapeutic ranges and approach and/or exceed toxic ranges due to drug tolerance.

Example of Drug Supporting Equations Above in Proof of Concept Study

Tramadol Example Calculation

TABLE 19

Tramadol pharmacokinetic parameters.
Tramadol

| | |
|---|---|
| Clearance (L × hr$^{-1}$ × kg$^{-1}$) | 0.480 |
| Volume of Distribution (L/kg) | 2.7 |
| Fractional Bioavailability | 0.725 |
| Fractional Rate Constant (hr$^{-1}$); "k" | 0.178 |
| Unbound Fraction (fp) | 0.80 |
| pKa | 9.4 |

TABLE 20

Donor information.

| Donor | Salivary pH (pHs) | Dose (mg) | Dosing Frequency (hr) | Weight (kg) |
|---|---|---|---|---|
| 0673 | 6.8 | 50 | 6 | 105.782 |
| 0604 | 5.5 | 50 | 8 | 81.720 |
| 0442 | 5.8 | 100 | 8 | 89.890 |

TABLE 21

Donor calculations.

| Donor | Donor Clearance (L/hr) Donor Clearance (L/hr) = Drug Clearance (L × hr$^{-1}$ × kg$^{-1}$) × Donor Weight (kg) | $DV_d$ (L) $DV_d$ (L) = $V_d$ (L) × Donor Weight (kg) |
|---|---|---|
| 0673 | $= 0.480 \times 105.782$ | $= 2.7 \times 105.782$ |
|  | $= 50.775$ L/hr | $= 285.6$ L |
| 0604 | $= 0.480 \times 81.72$ | $= 2.7 \times 81.720$ |
|  | $= 39.226$ L/hr | $= 220.6$ L |

TABLE 21-continued

Donor calculations.

| Donor | Donor Clearance (L/hr) Donor Clearance (L/hr) = Drug Clearance (L × hr$^{-1}$ × kg$^{-1}$) × Donor Weight (kg) | $DV_d$ (L) $DV_d$ (L) = $V_d$ (L) × Donor Weight (kg) |
|---|---|---|
| 0442 | = 0.480 × 89.89<br>= 43.148 L/hr | = 2.7 × 89.890<br>= 242.7 L |

TABLE 22

Calculated steady state maximum plasma tramadol concentration.

$$C_{ss}\text{max} = \frac{F \times \text{dose}/1 - e^{-kt}}{DV_d}$$

| Donor 0673 | Donor 0604 | Donor 0442 |
|---|---|---|
| $= \dfrac{0.725 \times 50/1 - e^{-(0.178 \times 6)}}{285.6}$ | $= \dfrac{0.725 \times 50/1 - e^{-(0.178 \times 8)}}{220.6}$ | $= \dfrac{0.725 \times 100/1 - e^{-(0.178 \times 8)}}{242.7}$ |
| = 193.3 ng/mL | = 216.6 ng/mL | = 393.4 ng/mL |

TABLE 23

Calculated steady state minimum plasma tramadol concentration.
$C_{ss}\text{ min} = C_{ss}\text{ max} \times e^{-kt}$

| Donor 0673 | Donor 0604 | Donor 0442 |
|---|---|---|
| = 193.387 × $e^{-(0.178 \times 6)}$ | = 216.387 × $e^{-(0.178 \times 8)}$ | = 393.430 × $e^{-(0.178 \times 8)}$ |
| = 66.4 ng/mL | = 52.0 ng/mL | = 94.7 ng/mL |

TABLE 24

Calculated saliva to plasma tramadol concentration ratio calculation.

$$S/P = \frac{1 + 10^{(pKa-pHs)} \times fp}{1 + 10^{(pKa-pHp)} \times fs}$$

| Donor 0673 | Donor 0604 | Donor 0442 |
|---|---|---|
| $= \dfrac{1 + 10^{(9.4-6.8)} \times 0.80}{1 + 10^{(9.4-7.4)} \times 1}$ | $= \dfrac{1 + 10^{(9.4-5.5)} \times 0.80}{1 + 10^{(9.4-7.4)} \times 1}$ | $= \dfrac{1 + 10^{(9.4-5.8)} \times 0.80}{1 + 10^{(9.4-7.4)} \times 1}$ |
| = 3.1 | = 62.9 | = 31.5 |

TABLE 25

Tramadol LC-MS/MS quantitation.

| Donor | Measured Saliva Tramadol Concentration (ng/mL) | Measured Plasma Tramadol Concentration (ng/mL) |
|---|---|---|
| 0673 | 375.6 | 104.1 |
| 0604 | 29926.5 | 376.6 |
| 0442 | 1302.5 | 70.4 |

TABLE 26

Oral fluid plasma equivalent calculation.

$$\text{Oral fluid plasma equivalent (ng/mL)} = \frac{\text{Measured oral fluid drug concentration (ng/mL)}}{\text{Calculated } S/P}$$

| Donor 0673 | Donor 0604 | Donor 0442 |
|---|---|---|
| $= \frac{375.6}{3.1}$ | $= \frac{29926.5}{62.9}$ | $= \frac{1302.5}{31.5}$ |
| = 118.7 ng/mL | = 475.5 ng/mL | = 41.2 ng/mL |

TABLE 27

Compliance analysis.

| Donor | $C_{ss}$ max (ng/mL) | $C_{ss}$ min (ng/mL) | Measured Tramadol Plasma Concentration (ng/mL) | Compliance | Tramadol Oral Fluid Plasma Equivalent (ng/mL) | Compliance | Agreement in Compliance |
|---|---|---|---|---|---|---|---|
| 0673 | 193.3 | 66.4 | 104.1 | Within | 118.7 | Within | Agree |
| 0604 | 216.3 | 52.0 | 376.6 | Above | 475.5 | Above | Agree |
| 0442 | 393.4 | 94.7 | 70.4 | Below | 41.2 | Below | Agree |

Expected steady state plasma drug range is calculated based on dosing regimen provided by donor. Maximum steady state concentrations may fall outside therapeutic ranges and approach and/or exceed toxic ranges due to drug tolerance.

Determination of Minimum Dosage Consumed Based on Oral Fluid Plasma Equivalent Once oral fluid plasma equivalent is calculated based on the quantitated oral fluid drug concentration by Eq. 8, assessment of the minimum dosage of a drug required to produce a corresponding oral fluid drug concentration is calculated.

Determination of minimum dosage consumed based on oral fluid plasma equivalent  Eq. 9

$$D_o = \frac{[(DV_d) \times C \times (K_a - K_{el})]}{F \times K_a(e^{-Kel \times t} - e^{-Ka \times t})}$$

$D_0$ = Original dose taken (mg)

$DV_d$ = Volume of distribution of donor (mL) (reference Eq. 2)

$C$ = Plasma drug concentration (mg/mL)

$K_a$ = Absorption constant of drug (referenced in literature)

$K_{el}$ = Elimination constant of drug (referenced in literature)

$F$ = Fractional bioavailability of drug (referenced in literature)

$t$ = Elapsed time between dosage and specimen collection (hr).

Example Supporting Minimum Dose Consumed Calculation Above in Proof of Concept Study

Oxycodone Example Calculation

TABLE 28

Oxycodone pharmacokinetic parameters.
Oxycodone

| | |
|---|---|
| Volume of Distribution (mL/kg) | 2000 |
| $K_a$ (hr$^{-1}$) | 3.5 |
| $K_{el}$ (hr$^{-1}$) | 0.174 |
| Fractional Bioavailability | 0.735 |

TABLE 29

Donor information.
Donor 0565

| | |
|---|---|
| Salivary pH (pH$_S$) | 6.4 |
| Weight (kg) | 118.040 |
| Measured Oral Fluid Concentration (ng/mL) | 217.1 |

TABLE 30

Donor compliance analysis.

| $C_{ss}$ max (ng/mL) | $C_{ss}$ min (ng/mL) | Measured Oxycodone Plasma Concentration (ng/mL) | Compliance | Oral Fluid Plasma Equivalent (ng/mL) | Compliance | Agreement in Compliance |
|---|---|---|---|---|---|---|
| 32.8 | 1.6 | 33.7 | Above | 42.0 | Above | Agree |

TABLE 31

Parameters for determination of minimum dosage consumed based on measured plasma drug concentration.
Donor 0565

| | |
|---|---|
| Measured Plasma Concentration (ng/mL) | 33.7 |
| Time Last Dose Taken | 13:00 |
| Time of Blood Collection | 14:23 |
| Time Elapsed Between Last Dose Taken and Blood Collection (hr) | 1.383 |

TABLE 32

Determination of minimum dosage consumed based on calculated plasma drug concentration.
Donor 0565

| | |
|---|---|
| Calculated Plasma Concentration (ng/mL) | 42.0 ng/mL (reference Eq. 8) |
| Time Last Dose Taken | 13:00 |
| Time of Oral Fluid Collection | 14:20 |
| Time Elapsed Between Last Dose Taken and Oral Fluid Collection (hr) | 1.333 |

TABLE 33

Determination of minimum dosage consumed based on plasma drug concentration.

| Measured Plasma Concentration | Oral Fluid Plasma Equivalent |
|---|---|
| $D_o = \dfrac{[(DV_d) \times C \times (K_a - K_{el})]}{F \times K_a(e^{-K_{el} \times t} - e^{-K_a \times t})}$ | $D_o = \dfrac{[(DV_d) \times C \times (K_a - K_{el})]}{F \times K_a(e^{-K_{el} \times t} - e^{-K_a \times t})}$ |

TABLE 34

Comparison to dosage provided by donor.

| Dose Taken Provided (mg) | Minimum Dosage Consumed Based on Measured Plasma Concentration (mg) | Compliance | Minimum Dosage Consumed Based on Oral Fluid Plasma Equivalent (mg) | Compliance | Agreement in Compliance |
|---|---|---|---|---|---|
| 10 | 13.2 | Above | 16.3 | Above | Agree |

Example Supporting Minimum Dose Consumed Calculation Above in Proof of Concept Study Hydrocodone Example Calculation

TABLE 35

Hydrocodone pharmacokinetic parameters.
Hydrocodone

| | |
|---|---|
| Volume of Distribution (mL/kg) | 4000 |
| $K_a$ (hr$^{-1}$) | 2.8 |
| $K_{el}$ (hr$^{-1}$) | 0.141 |
| Fractional Bioavailability | 0.7 |

TABLE 36

Donor information.
Donor 0476

| | |
|---|---|
| Salivary pH (pH$_S$) | 7.2 |
| Weight (kg) | 84.898 |
| Measured Oral Fluid Concentration (ng/mL) | 4.5 |

TABLE 37

Donor compliance analysis.

| $C_{ss}$ max (ng/mL) | $C_{ss}$ min (ng/mL) | Measured Oxycodone Plasma Concentration (ng/mL) | Compliance | Oral Fluid Plasma Equivalent (ng/mL) | Compliance | Agreement in Compliance |
|---|---|---|---|---|---|---|
| 23.7 | 8.2 | 3.2 | Below | 4.5 | Below | Agree |

TABLE 38

Parameters for determination of minimum dosage consumed based on measured plasma drug concentration.
Donor 0476

| | |
|---|---|
| Measured Plasma Concentration (ng/mL) | 3.2 |
| Time Last Dose Taken | 07:00 |
| Time of Blood Collection | 13:03 |
| Time Elapsed Between Last Dose Taken and Blood Collection (hr) | 6.050 |

TABLE 39

Determination of minimum dosage consumed based on oral fluid plasma equivalent.
Donor 0476

| | |
|---|---|
| Oral Fluid Plasma Equivalent (ng/mL) | 4.5 ng/mL (reference Eq. 8) |
| Time Last Dose Taken | 07:00 |
| Time of Oral Fluid Collection | 12:50 |
| Time Elapsed Between Last Dose Taken and Oral Fluid Collection (hr) | 5.833 |

TABLE 40

Determination of minimum dosage consumed based on plasma drug concentration.

| Measured Plasma Concentration | Oral Fluid Plasma Equivalent |
|---|---|
| $D_o = \dfrac{[(DV_d) \times C \times (K_a - K_{el})]}{F \times K_a(e^{-K_{el} \times t} - e^{-K_a \times t})}$ | $D_o = \dfrac{[(DV_d) \times C \times (K_a - K_{el})]}{F \times K_a(e^{-K_{el} \times t} - e^{-K_a \times t})}$ |
| $= \dfrac{[(4000 \text{ mL/kg} \times 84.898 \text{ kg}) \times (3.2 \text{ ng/mL} \times 1 \times 10^{-6}\text{ng}) \times (2.8 - 0.141)]}{0.7 \times 2.8(e^{-0.141 \times 6.050} - e^{-2.8 \times 6.050})}$ | $= \dfrac{[(4000 \text{ mL/kg} \times 84.898 \text{ kg}) \times (4.5 \text{ ng/mL} \times 1 \times 10^{-6}\text{ng}) \times (2.8 - 0.141)]}{0.7 \times 2.8(e^{-0.141 \times 5.833} - e^{-2.8 \times 5.833})}$ |
| = 3.5 mg | = 4.4 mg |

TABLE 41

Comparison to dosage provided by donor.

| Dose Taken Provided (mg) | Minimum Dosage Consumed Based on Measured Plasma Concentration (mg) | Compliance | Minimum Dosage Consumed Based on Oral Fluid Plasma Equivalent (mg) | Compliance | Agreement in Compliance |
|---|---|---|---|---|---|
| 7.5 | 3.5 | Below | 4.4 | Below | Agree |

Although the technology has been described in language that is specific to certain structures and materials, it is to be understood that the invention defined in the appended claims is not necessarily limited to the specific structures and materials described. Rather, the specific aspects are described as forms of implementing the claimed invention. Because many embodiments of the invention can be practiced without departing from the spirit and scope of the invention, the invention resides in the claims hereinafter appended. Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques. Moreover, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

What is claimed:

1. A method for determining a donor's adherence to a dosing regimen, the method comprising the steps of:
   collecting a sample of oral fluid from the donor;
   determining the pH of the oral fluid sample;
   readying the sample for transport and analysis by placing the sample in an appropriate buffer, and sealing and packing the sample;
   determining a concentration of the drug in the in the oral fluid sample;
   calculating an expected plasma steady state minimum drug concentration ($C_{ss}$min) and an expected plasma steady state maximum drug concentration ($C_{ss}$max);
   calculating an equivalent expected oral fluid steady state minimum drug concentration (Smin) and an expected oral fluid steady state maximum drug concentration (Smax) using $C_{ss}$min and according to the following steps:
   if the drug is an acidic drug, determine Smin and Smax using Eq. 5 by inputting $C_{ss}$min and $C_{ss}$max for P and solving for Smin and Smax (S):

$$S/P = [1+10^{(pH_s - pKa)} \times fp]/[1+10^{(pH_p - pKa)} \times fs]; \text{ and} \qquad \text{Eq. 5:}$$

if the drug is a basic drug, determine Smin and Smax using Eq. 6 by inputting $C_{ss}$min and $C_{ss}$max for P and solving for Smin and Smax (S):

$$S/P = [1+10^{(pKa - pH_s)} \times fp]/[1+10^{(pKa - pH_p)} \times fs]; \qquad \text{Eq. 6:}$$

wherein:
   $pH_s$ is a pH of saliva to be determined at the time of collection;
   $pH_p$ is a pH of plasma;
   pKa is a dissociation constant of the drug;
   fp is a free fraction of the drug in plasma; and
   fs is free fraction of the drug in saliva; and
   determining whether measured oral fluid drug concentration of the donor complies with the dosing regimen of the drug, at steady state, if the measured oral fluid drug concentration is within the range between Smax and Smin, wherein the step of determining the oral fluid drug concentration comprises preparing the sample for toxicological measurement of drug content and extracting the drug from the sample using mixed-mode cationic exchange columns.

2. The method of claim 1 wherein the dosing regimen comprises a plurality of drugs.

3. The method of claim 1 further comprising the step of collecting a predefined volume of oral fluid from the donor.

4. The method of claim 1 wherein the pH is determined by providing visual indicia of the pH.

5. The method of claim 1 wherein the predefined volume of the sample is collected with a simultaneous measurement of the sample pH.

6. The method of claim 1 wherein the step of determining the drug comprises using Liquid Chromatography Tandem Mass Spectrometry.

7. The method of claim 1 further comprising evaluating steady state drug levels via oral fluid drug measurements.

8. The method of claim 1 further comprising comparing measured oral fluid concentration with an expected oral fluid steady state range based on the prescribed dosing regimen.

* * * * *